US008834535B2

(12) United States Patent
McClintock

(10) Patent No.: US 8,834,535 B2
(45) Date of Patent: Sep. 16, 2014

(54) ANTERIOR VERTEBRAL PLATE WITH CLOSED THREAD SCREW

(75) Inventor: Larry E. McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 1407 days.

(21) Appl. No.: 11/700,242

(22) Filed: Jan. 31, 2007

(65) Prior Publication Data

US 2008/0234751 A1 Sep. 25, 2008

(51) Int. Cl.
*A61B 17/80* (2006.01)
*A61B 17/84* (2006.01)
*A61B 17/70* (2006.01)
*A61B 17/86* (2006.01)

(52) U.S. Cl.
CPC ......... *A61B 17/7059* (2013.01); *A61B 17/8635* (2013.01); *A61B 17/8033* (2013.01)
USPC ........................................................ 606/291

(58) Field of Classification Search
USPC ............... 606/86 B, 280, 289, 104, 290–291, 606/309–310, 319; 411/301, 399, 411, 437
See application file for complete search history.

(56) References Cited

U.S. PATENT DOCUMENTS

| | | | | |
|---|---|---|---|---|
| 1,177,810 A | * | 4/1916 | Rogness | 411/399 |
| 2,419,555 A | * | 4/1947 | Fator | 411/387.3 |
| 3,604,487 A | * | 9/1971 | Gilbert | 81/443 |
| 3,711,138 A | * | 1/1973 | Davis | 403/408.1 |
| 5,531,554 A | * | 7/1996 | Jeanson et al. | 411/399 |
| 5,601,553 A | * | 2/1997 | Trebing et al. | 606/86 B |
| 6,261,291 B1 | * | 7/2001 | Talaber et al. | 606/281 |
| 6,730,091 B1 | * | 5/2004 | Pfefferle et al. | 606/70 |
| 6,780,186 B2 | * | 8/2004 | Errico et al. | 606/71 |
| 2002/0065517 A1 | * | 5/2002 | Paul | 606/69 |
| 2004/0068319 A1 | * | 4/2004 | Cordaro | 623/17.11 |
| 2005/0165400 A1 | * | 7/2005 | Fernandez | 606/69 |
| 2005/0192578 A1 | * | 9/2005 | Horst | 606/69 |
| 2006/0100626 A1 | * | 5/2006 | Rathbun et al. | 606/69 |
| 2006/0235400 A1 | * | 10/2006 | Schneider | 606/69 |
| 2008/0177330 A1 | * | 7/2008 | Ralph et al. | 606/290 |
| 2009/0143824 A1 | * | 6/2009 | Austin et al. | 606/280 |

FOREIGN PATENT DOCUMENTS

WO  WO 2005018472 A1 * 3/2005  ............ A61B 17/80

* cited by examiner

*Primary Examiner* — Christian Sevilla
(74) *Attorney, Agent, or Firm* — Carter, DeLuca, Farrell & Schmidt, LLP

(57) ABSTRACT

Provided is a novel system that includes a low profile anterior vertebral body plate and closed thread screws for the fixation and stabilization of the cervical spine, the closed thread screw having an integral novel screw locking mechanism of an uppermost closed thread having a flat pitch, which engages and attaches the plate so as to lock the screw into the plate until an intentional, simultaneous combination of outward pulling force and counter-clockwise torque is applied to release the closed thread screw from the plate. Also provided is a method of stabilizing cervical vertebrae using the disclosed system.

18 Claims, 4 Drawing Sheets

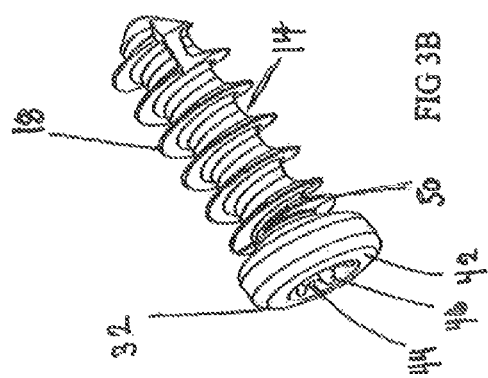
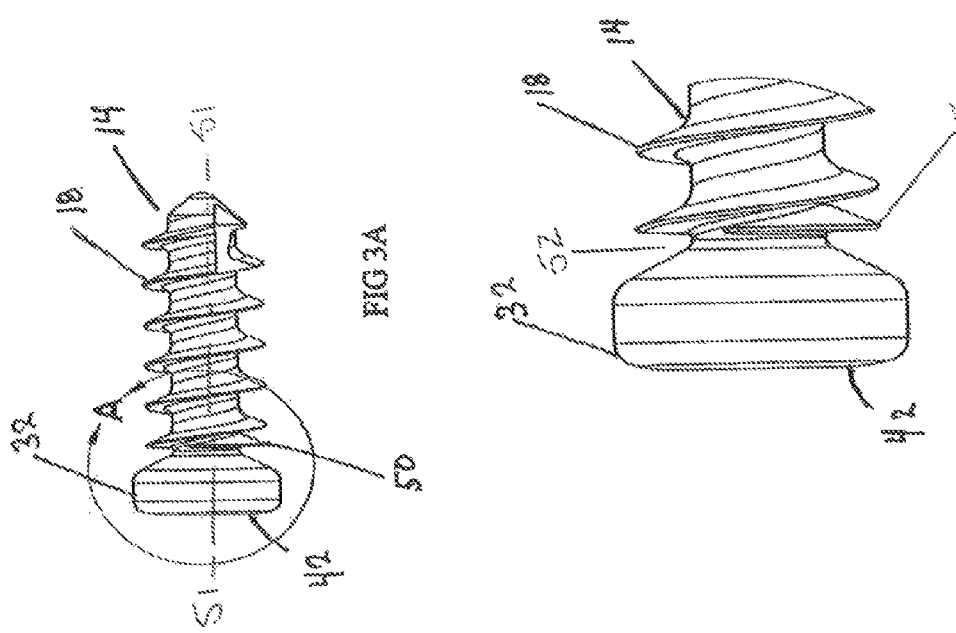

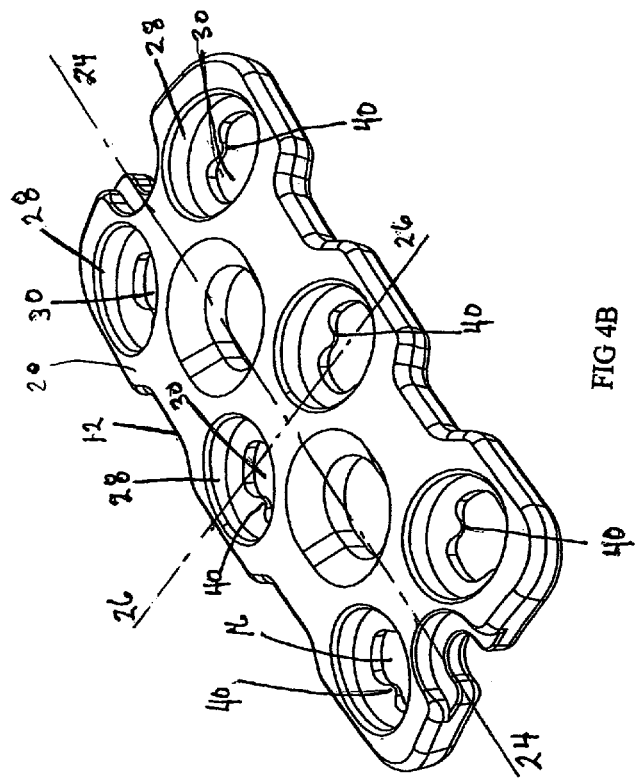
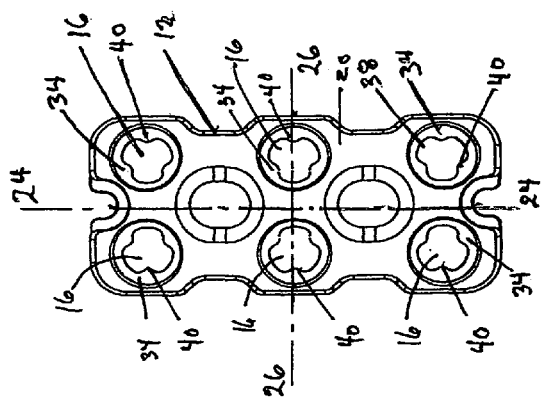
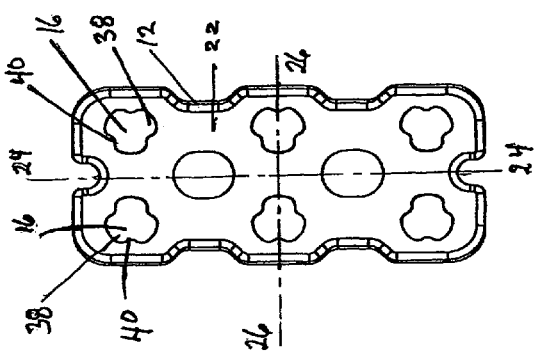

ANTERIOR VERTEBRAL PLATE WITH CLOSED THREAD SCREW

BACKGROUND OF THE INVENTION

1. Technical Field

The present invention relates to devices and methods for use in orthopedic spine surgery. In particular, the present invention relates to a system that provides a low profile anterior vertebral body plate and closed thread screws for the fixation and stabilization of the cervical spine, the closed thread screw in combination with the anterior vertebral plate providing a novel screw locking mechanism that requires no additional locking elements.

2. Background Art

Disease, the effects of aging, or physical trauma resulting in damage to the spine has been treated in many instances by fixation or stabilization of the effected vertebra. The use of plates and screws for fixation and stabilization of the cervical vertebra has been widely accepted as a reliable practice and has proven to be highly successful clinically.

The various plates, which are attached to the anterior vertebral bodies of the spinal column by bone screws have some common features such as relatively planar body profiles that define multiple holes or slots through which the screws fit and are threaded into the bone. Various means have been used to prevent the screws from becoming loose or detached from their necessary secured or locked attachment to the vertebral plate. Among the differences between the conventionally used plates and screws is the manner in which the screws are locked into place in the hole or slot of the plate after the screws have been secured to the bone.

These conventional devices can be generally grouped into three basic categories with regard to how the screws are captured or secured in the plates.

Early plate designs were standard bone plates having holes through which screws were passed and screwed into the bone. These plates had no special provision for attaching the screws to the plate and as such were susceptible to having the screws back out of the plate over time. There have been clinically reported instances of screws backing out of these type plates with resulting surgical complications. Due to the potential and actual unreliable performance of such plates, the need for secure fixation of the screw to the plate as well as to the bone is now considered a basic requirement for vertebral plates. Due to the lack of predictable security of the screw to the plate, plates which do not secure the screw relative to the plate have fallen out of favor and virtually disappeared from use.

Efforts have been made to secure the screws relative to the plates. In one design the screw head contains a threaded hole configured to receive a set screw. After the screw has been driven into bone and the head is seated in the plate hole, the set screw is inserted into the receiving hole of the screw head. The set screw is tapered to cause the screw head to expand and frictionally engage the wall of the plate hole, thereby resisting forces which tend to cause the screw to back out. While such mechanisms have worked to some degree, the addition of a small additional part, the set screw, at the time of surgery presents the potential hazard of dropping the set screw into the surgical field or otherwise misapplying the set screw to the screw head, for example, cross threading.

An alternative approach has been to provide features in the plate, which are specifically designed to hold the screw in position once the screw is inserted through the plate and screwed into the bone. One direction taken in this effort has been to design plates that incorporate or attach individual retaining rings or snap features associated with each plate hole configured to hold the inserted screw in place relative to the plate. These plates are very common and widely used; however, an inherent problem associated with such plates is the use of the additional very small retaining elements that can become disengaged from the plate and migrate into the surrounding soft tissues. Further, difficulty experienced in accessing and disengaging the small locking elements and removing the screws from this type of plate has caused some concern for the continued use of such plates. A similar approach involves individual cams associated with each plate hole, which when rotated apply friction pressure to the screw head in an attempt to resist back out.

Another approach is to add a cover to the plate after the screws have been placed. Such a design undesirably adds steps to the surgical procedure, thickness or height to the overall construct, and is susceptible to misapplication. Yet another direction taken in this effort to provide plates with locking elements is to provide dedicated overlying features, which are attached to the top side of the vertebral plate for the purpose of covering at least a portion of the screw head and thereby holding the screw in a seated and locked position. Generally these plates are designed to provide a variety of screw covering features that are pre-attached to the plate, and which can be selectively slid or rotated into position once it has been inserted. In some devices, such covering plates cover multiple screw heads. These plates typically require an increase in the overall composite thickness of the plate in order to accommodate the additional locking feature attached to the top side of the plate. This is a particularly unacceptable condition due to the use of such plates in an area of the spine where a thin, smooth surfaced profile for the plate assembly is preferred. Another major problem with such plates is that the overlying locking element cannot always be properly positioned over the screw head if the screw shaft was, due to anatomical necessity, positioned through the plate and into the bone at an angle such that the screw head does not fully seat in the plate recess provided on the top side of the plate. Further, when one of the overlying locking elements of such a plate loosens or becomes disengaged it is then free to float away from the top side of the plate and migrate into the soft tissue adjacent to the top side of the vertebral plate.

Yet another approach is to provide machine threads in the plate hole with corresponding threads on the screw head. Thus the screw has a first, bone engaging thread on its shaft and a second machine thread on the screw head. As the thread shaft is screwed into bone the screw head approaches the plate hole and the machine thread engages the thread in the hole. Aside from the fact that there is nothing to prevent the same forces that urge the screw to back out of bone to have the same effect on the machine thread engagement, such an arrangement does not provide adequate clinical flexibility. First there is no assurance that the lead in thread of the machine thread will match up with the plate hole thread when the screw head reaches the hole, raising the possibility of cross threading. Second, the machine thread in the plate hole does not allow various angular positions between the screw and the plate, as the threads must match up and engage when the screw head reaches the hole. As to the latter point, one plate provides a threaded ring in the plate hole, which is intended to allow the head to assume a variety of angular positions.

There is therefore, an unfulfilled need for an anterior cervical plate system that can maintain a relatively low profile, as found in the non-locking plates while providing the security of a locking plate system. Further there is a need for a vertebral plate that does not have additional separate locking elements with the predictable problems of locking elements becoming disengaged from the plate and migrating away from the top side of the plate into the surrounding soft tissue.

SUMMARY OF THE DISCLOSURE

The present invention meets the above identified need by providing a low profile anterior vertebral body plate, which is secured to the underlying bone using novel closed thread screws.

Also provided is a low profile anterior vertebral body plate, which is secured to the underlying bone using novel closed thread screws having an integrally formed locking element that engages the plate so as to secure and lock the screw into a set position relative to said plate.

Also provided is a low profile anterior vertebral body plate, which is secured to the underlying bone using novel closed thread screws, each of the screws having a screw head and an upper most final thread having a flat pitch so as to discontinue the upward spiral pitch of lower oriented screw threads.

Also provided is a low profile anterior vertebral body plate, which is secured to the underlying bone using novel closed thread screws, each of the screws having a screw head and an upper most final thread having a flat pitch so as to discontinue the upward spiral pitch of lower oriented screw threads, the diameter of the final flat pitch thread being sufficient to engage the inner edge or flange of the screw holes of the plate.

Also provided is a novel bone screw having a closed thread formed at the upper limit of the threaded portion of the bone screw, the closed thread being capable of circumferentially engaging the inner edge or flange of a bone screw hole in a plate so as to form a locking relationship therewith.

Also provided is a novel bone screw having at least one loosening/removing tool engaging structure defined in the surface of the screw head.

Also provided is a novel low profile anterior vertebral body plate system including a plate and closed thread screws, the interaction between the closed thread screw and plate providing a locking mechanism not requiring an additional locking element.

Also provided is a method of stabilizing spinal vertebrae, the method including providing a low profile anterior vertebral body plate, which is securely attached to the underlying bone of adjacent vertebrae using novel closed thread screws so as to hold one attached vertebra in a fixed position relative to the adjacent attached vertebra.

Also provided is a kit, which includes at least one low profile anterior vertebral body plate and a corresponding set of novel closed thread screws.

BRIEF DESCRIPTION OF THE DRAWINGS

The foregoing and other features of the novel low profile anterior vertebral plate system will become apparent to one skilled in the art to which the disclosed system and devices relate upon consideration of the following description of exemplary embodiments with reference to the accompanying drawings, wherein:

FIGS. 3A-C show a side view, an isometric view, a closed thread portion detail view of the closed thread screw.

FIGS. 4A-C show a top view, isometric view, and a bottom view of the anterior vertebral plate.

DETAILED DESCRIPTION OF PREFERRED EMBODIMENTS

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

Figures 1, 2:
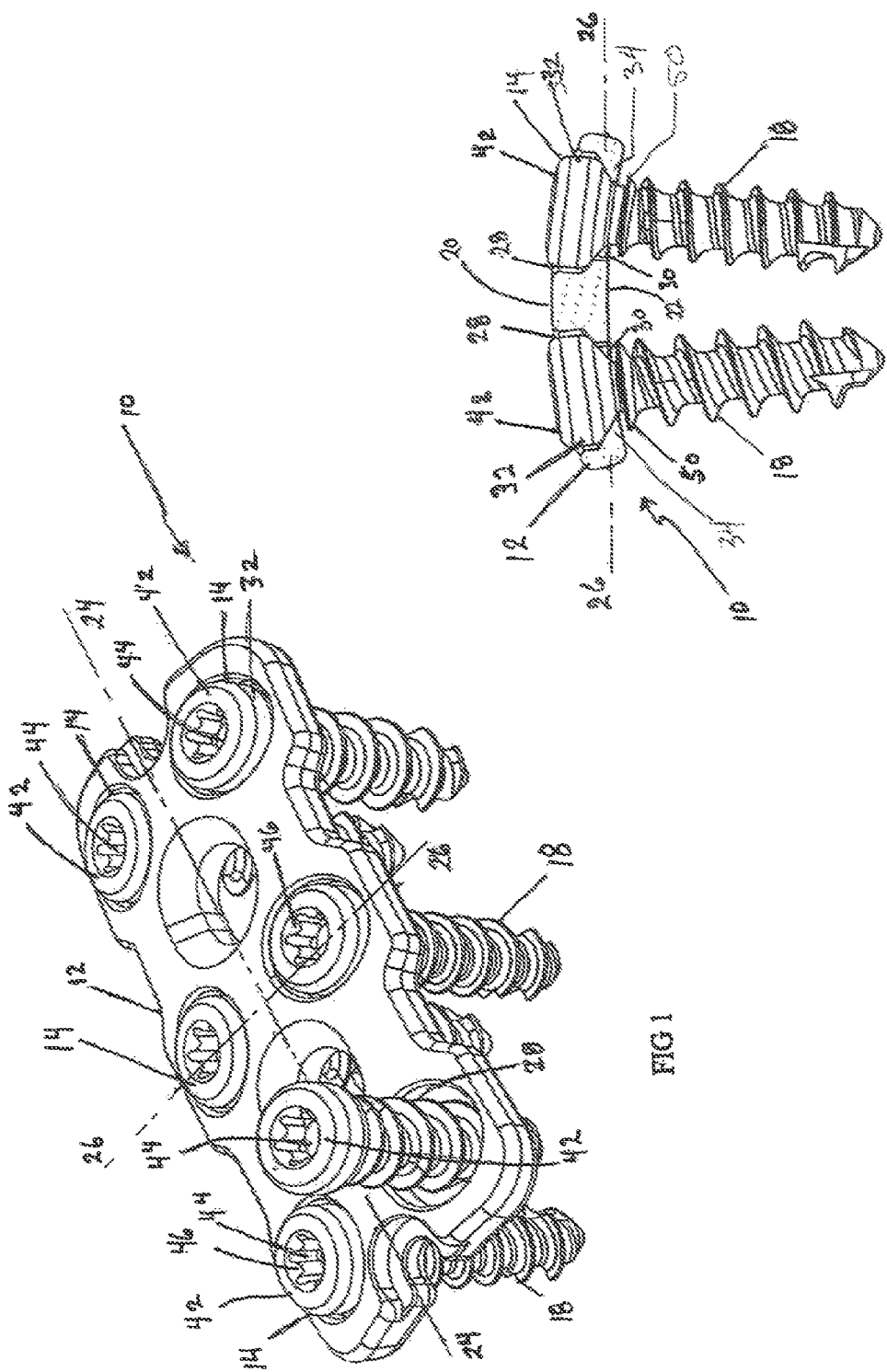
FIG. 1 shows an isometric view of the plate system with five of the closed thread screws fully seated within the plate holes and a sixth closed thread screw partially inserted in a plate hole.
FIG. 2 shows a transverse cross sectional view of the plate system through two of the fully seated closed thread screws.

The system, as generally shown at 10 in FIGS. 1 and 2, includes a low profile anterior vertebral body plate 12 that, when implanted in a patient, can be secured to the underlying bone using closed thread bone screws 14, which are shown at 14 in FIGS. 1, 2, 3A-C, and 5. The vertebral body plate 12, as best shown in FIGS. 1, 2, and 4A-C can be provided as an elongated, low profile, plate structure that defines at least one and preferably multiple screw holes 16, which are sized and configured to permit through passage for the threaded portion 18 of the bone screw 14 from the plate upper surface 20 to the plate lower surface 22.

As shown in FIGS. 1, 2, and 4B the plate 12 can be configured to be generally planar; however, the plate preferably will be formed to have arcuate upper and lower surfaces 20, 22, arcing along both the longitudinal axis 24 as well as the transverse axis 26 of the plate 12. This arcing of the plate surface provides a better conformational fit to the anterior surface of the vertebrae to which the plate is to be attached. Each of the screw holes 16, which are defined as through passages in the plate 12, is configured at the upper portion 28 to be generally circular and sized to circumferentially surround the screw head when the screw 14 is fully seated in the plate 12. The lower portion 30 of the screw hole 16 is configured to have an inwardly projecting flange 34 having a generally inward slanting or rounded concave shaped surface that is complementary to the shape of the underside 36 of the screw head 32. The inner most edge of the inwardly projecting flange 34, as best shown in FIGS. 4A-C defines a non-continuous circular shaped exit portal 38 for the screw hole 16 lower portion 30. The non-continuous circular shape of the exit portal 38 is periodically interrupted by inwardly projecting thread engaging projections 40. As best shown in FIG. 4B, the thread engaging projections 40 can be formed to be of a lesser thickness than the other portions of the flange 34. This lesser thickness of the thread engaging projections 40 relative to the average thickness of the flange 34 provides a more accommodating surface edge by which the plate hole 16 and the threaded portion 18 of the screw 14 can become threadably engaged and interact during insertion, removal, and locking of the screw 14 to the plate 12.

Figure 5:
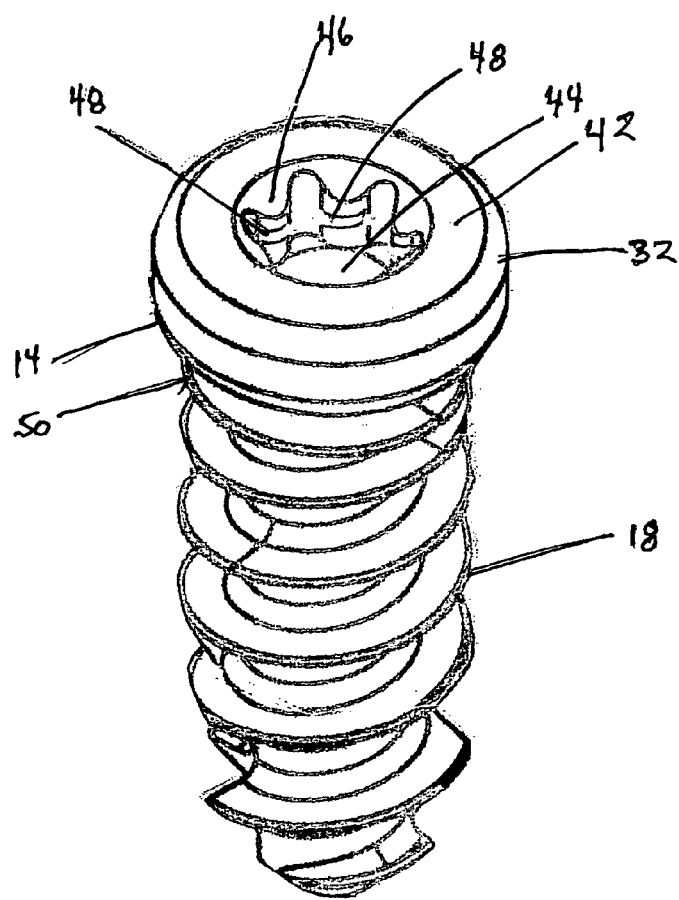
FIG. 5 shows an exemplary embodiment of a closed thread screw, the screw head having at least one loosening/removing tool engaging structure defined in the tool receptacle, the tool receptacle being defined as a recess in the upper surface of the screw head.

As best shown in FIGS. 1 and 5, the upper surface 42 of the screw head 32 can define a tool receiving recess 44, which is sized and configured to operationally engage a tightening/loosening/removal tool as needed. Tool gripping elements 46 can be defined on the inner surface of the tool receiving recess 44, the gripping elements 46 being of a complementary shape to the tool being used. Any of a variety of known or novel shapes for gripping elements 46 can be used so long as they are complimentary to the shape of the tool employed. As shown in the non-limiting exemplary embodiment of the bone screw 14 depicted in FIG. 5, the screw head can be provided with at least one loosening/removing tool engaging surface 48, which can be defined in the tool receiving recess 44. This removing tool engaging surface 48 can be of any configuration and can be located within the tool receiving recess 44 or on any accessible surface of the screw head 32 so long as the engaging surface is configured and positioned to facilitate the screw head 32 being grasped and pulled in an upward direction away from the plate 12 during the simultaneous application of reverse torque to the effect the screw and plate disengagement and removal process.

The closed thread screw 14 includes a single closed thread 50 as the upper most thread of the screw threaded portion 18. The closed thread 50 has a virtually flat pitch that rapidly transitions from the conventional degree of pitch provided in the upward spiral of the lower threaded portion 18 along a long axis 51 of the screw 14. This transition from a conventional upward spiraling thread pitch to the flat pitch of the singular closed thread immediately beneath the screw head 32 is best shown in FIG's. 2 and 3A-C.

An annular gap 52 exists between the closed thread 50 and the underside of screw head 32. The annular gap 52 is dimensioned such that when screw 14 is advanced through screw hole 16 the screw hole flange 32 is disposed in the annular gap 52 (FIG. 2) so as to effectively lock screw 14 to the plate 12. The annular gap 52, in combination with the closed thread 50, permits the screw 14 to rotate about long axis 51 in relation to the plate 12 and prohibits screw 14 from re-engaging the screw hole flange 34 without the intentional application of both an outward pulling force and a counter-clockwise application of torque as described hereinbelow.

Upon insertion and the application of torque to the screw, the bone screw 14 is drawn by the normal pitched threads of the threaded portion 18 of the screw 14 through the screw hole 16 and into the underlying bone material until the final flat pitched or closed thread 50 advances past the flange 34 at the bottom of the bone screw hole 16. Due to the abrupt change from normal thread pitch to the flat pitch of the closed thread 50, the screw 14 transition past the flange 34 is met with increased resistance to the applied torque forces. This increased resistance provides a tactile indicator that the closed thread 50 has engaged the flange 34. The resistance is quickly overcome as the single closed thread 50 is drawn below the flange 34 and is no longer engaged therewith. Additional screw rotation continues to draw the screw into the bone and pulls the screw head 32 into a fully seated position in the screw hole 16 of the plate 12. The additional rotation and resulting further advancement of the screw 14 into the underlying bone serves to pull the screw head 32 against the screw hole flange 34 and thus forces the plate 12 securely against the surface of the underlying bone. Because of the flat pitch of the closed thread 50, a counter-clockwise rotation of the screw 14 will not automatically reengage the closed thread 50 to the screw hole flange 34 as it would for a normal pitched thread. Only a counter-clockwise rotation of the screw 14 coupled with a simultaneous outward pulling force on the screw head 32 can cause the closed thread 50 to re-engage the screw hole flange 34 in the screw removal process. Thus, the screw 14 can be inwardly rotated to a point where the closed thread 50 is seated below the screw hole flange 34 so as to effectively lock the screw 14 to the plate 12, a locked position that can only be overcome by the intentional application of both an outward pulling force and a counterclockwise application of torque.

Further, the curvate underside 36 of the screw head 14 during screw insertion enables articulation of the screw head with the complimentary conformation of the lower portion 30 of the screw hole 16. This capacity for the screw head 32 to articulate during the screw insertion process and then be locked into position relative to the plate 12 enables the screw to be polyaxial in relationship to the plate as necessary. This polyaxial feature is a distinct advantage for a secure attachment to the underlying bone.

The above described method of use of the system 10 can be employed as a method of stabilizing or fixing injured or diseased vertebrae and if necessary, multiple devices or a device, which is elongated beyond the examples depicted herein, can be employed as necessary. Importantly, a mere reversal of rotational torque on the screw head using a tool designed to provide that reversed torque will not disengage the closed thread screw 14 from the plate 12. Only an intentional outward pull of the screw provided simultaneously with the application of a reversed torque can cause the flat pitch closed thread to reengage the flange and thus be removed from the plate 12.

While the device as described herein can be preferably used to attach to the anterior surface of cervical vertebrae and is configured to be capable of stabilizing cervical vertebrae, it is within the inventors' understanding that the plate can be configured and adapted to conform to any implantable surgical plate requirement to provide a low profile plate capable of securing and stabilizing any injured or diseased bone.

The device 10 can be manufactured as integral components by methods known in the art, to include, for example, molding, casting, forming or extruding, and machining processes. The components can be manufactured using materials having sufficient strength, resiliency and biocompatibility as is well known in the art for such devices. By way of example only, suitable materials can include implant grade metallic materials, such as titanium, cobalt chromium alloys, stainless steel, or other suitable materials for this purpose. It is also conceivable that some components of the device can be made from plastics, composite materials, and the like.

It is also within the concept of the inventors to provide a kit, which includes at least one of the vertebral plate and closed thread screw systems disclosed herein. The kit can also include additional orthopedic devices and instruments; such as for example, instruments for tightening or loosening the bone screws, spinal rods, hooks or links and any additional instruments or tools associated therewith. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. A bone plate system, comprising:
a plate having a proximal surface and a distal surface, the plate defining at least two bone screw holes extending through the plate along an axial axis, the bone screw holes having a generally circular proximal portion and a distal portion having an inwardly directed flange with a non-continuous circular configuration interrupted by a plurality of thread engaging projections; and
at least two screws configured and dimensioned for position within the at least two bone screw holes, the screws each having a head, and a threaded shank extending from the head along a longitudinal shank axis, the threaded shank including a first threaded portion having a first pitch extending along a plane orthogonal in relation to the shank axis and defining an annular gap between the head and the first threaded portion, and a second threaded portion having a second pitch extending along a plane subtending an acute angle with respect to the shank axis, wherein the flange is configured and dimensioned to engage the threaded shank, and defines a thickness extending along the axial axis, the thickness of the flange being non-uniform, the first threaded portion of each shank being configured and dimensioned for engagement with, and thereafter, passage beneath the thread engaging projections of the flange of the screw hole, wherein the flange is disposed within the annular gap, thereby permitting the screw to rotate about the longitudinal shank axis of the screw with respect to the plate and inhibiting axial movement of the screw.

2. The bone plate system of claim 1, wherein the longitudinal shank axis of one of the screws is capable of polyaxial alignment with respect to the axial axis of one of the least two bone screw holes of the plate.

3. The bone plate system of claim 1, wherein the device is an anterior vertebral body plate.

4. The bone plate system of claim 1, wherein the proximal and distal surfaces of the plate have a curvate configuration.

5. The bone plate system of claim 4, wherein the proximal and distal surfaces of the plate are curved along a transverse axis of the plate.

6. The bone plate system of claim 4, wherein the proximal and distal surfaces of the plate are curved along a longitudinal axis of the plate.

7. The bone plate system of claim 1, wherein the head of each screw has a curvate underside of complimentary configuration to the inwardly directed flange, wherein the head of each screw and the flange is capable initially of rotational interaction such that the screws, when fully seated and locked into position within the plate, are capable of being polyaxial relative to each other.

8. A method of stabilizing a vertebral body, the method comprising:
providing a bone plate system according to claim 1;
surgically accessing an anterior surface of a vertebral body in need of stabilization; and
positioning the bone plate and attaching same to the vertebral body using at least one of the at least two screws.

9. A kit comprising at least one system according to claim 1 and at least one other tool or instrument for use in orthopedic surgery.

10. The bone plate system of claim 1, wherein the thickness of the thread engaging projections is less than the thickness defined by remaining portions of the flange.

11. The bone plate system of claim 1, wherein the head of each screw includes an engaging surface extending radially inward, the engaging surface being configured and dimensioned to enable application of proximally directed force to the screws to facilitate removal thereof.

12. A bone plate system, comprising:
a plate including a proximal surface, a distal surface, and a bone screw hole extending through the plate between the proximal and distal surfaces, the bone screw hole including a flange having a plurality of radial projections; and
a bone screw configured and dimensioned for positioning within the bone screw hole, the bone screw including a head, and a threaded shank extending from the head along a longitudinal axis, the shank including a first threaded portion having a first pitch extending along a plane orthogonal in relation to the longitudinal axis and defining an annular gap between the head and the first threaded portion, such that rotation of the bone screw causes engagement of the first threaded portion with the plurality of projections, and thereafter, passage of the first threaded portion distally beyond the plurality of projections, wherein the flange is disposed within the annular gap, thereby permitting the screw to rotate about the longitudinal shank axis of the bone screw with respect to the plate and inhibiting axial movement along the longitudinal axis with respect to the plate.

13. The bone plate system of claim 12, wherein the shank of the bone screw further includes a second threaded portion having a second pitch different from the first pitch.

14. The bone plate system of claim 13, wherein the second pitch extends along a plane subtending an acute angle with respect to the longitudinal axis.

15. The bone plate system of claim 13, wherein the first threaded portion is positioned proximally of the second threaded portion.

16. The bone plate system of claim 12, wherein the plurality of projections define a plurality of gaps between adjacent projections.

17. The bone plate system of claim 12, wherein the flange defines a non-uniform thickness.

18. The bone plate system of claim 12, wherein at least one of the proximal and distal surfaces of the plate includes a curvate configuration.

* * * * *